US008925368B2

(12) United States Patent
Kim et al.

(10) Patent No.: US 8,925,368 B2
(45) Date of Patent: Jan. 6, 2015

(54) MULTI-DIMENSIONAL GAS CHROMATOGRAPHY CHIP WITH MODULATOR

(71) Applicants: Sang-Goo Kim, Seoul (KR); Sung-Min Lim, Seoul (KR)

(72) Inventors: Sang-Goo Kim, Seoul (KR); Sung-Min Lim, Seoul (KR)

(73) Assignee: Korea Basic Science Institute, Yuseong-gu (KR)

( * ) Notice: Subject to any disclaimer, the term of this patent is extended or adjusted under 35 U.S.C. 154(b) by 52 days.

(21) Appl. No.: 13/717,954

(22) Filed: Dec. 18, 2012

(65) Prior Publication Data
US 2014/0157865 A1     Jun. 12, 2014

(30) Foreign Application Priority Data
Dec. 11, 2012    (KR) .......................... 10-2012-0143837

(51) Int. Cl.
*G01N 30/02*     (2006.01)
*G01N 30/46*     (2006.01)
*G01N 30/60*     (2006.01)

(52) U.S. Cl.
CPC .......... *G01N 30/463* (2013.01); *G01N 30/6095* (2013.01)
USPC .......................................................... 73/23.4

(58) Field of Classification Search
CPC . G01N 30/463; G01N 30/6095; G01N 30/60; G01N 30/466; G01N 30/6043
USPC .............. 73/23.35, 23.4, 23.41, 23.42; 95/82; 96/101; 422/89
See application file for complete search history.

(56) References Cited

U.S. PATENT DOCUMENTS

| 3,581,573 A | * | 6/1971 | Purcell et al. | ............... | 73/863.11 |
| 4,935,040 A | * | 6/1990 | Goedert | ....................... | 73/23.22 |
| 5,205,845 A | | 4/1993 | Sacks | | |

* cited by examiner

*Primary Examiner* — Daniel S Larkin
*Assistant Examiner* — Jamar Ray
(74) *Attorney, Agent, or Firm* — Chapin IP Law, LLC

(57) ABSTRACT

Disclosed is a multi-dimensional gas chromatography chip with a modulator. The multi-dimensional gas chromatography chip includes a chip body including first to third substrates; first micro channel pattern parts including first micro channels; second micro channel pattern parts including second micro channels; a gas inlet to supply a mobile phase; a gas outlet to discharge the mobile phase; position alignment markers formed on one surface of the first substrate, both surfaces of the second substrates and one surface of the third substrate; a first stationary phase spin-coated between the first and second substrates and a second stationary phase spin-coated between the second and third substrates; and a modulator provided in a region serving as an inlet side of the first micro channel pattern parts as well as an outlet side of the second micro channel pattern parts.

8 Claims, 7 Drawing Sheets

(a)

(b)

MULTI-DIMENSIONAL GAS CHROMATOGRAPHY CHIP WITH MODULATOR

CROSS-REFERENCE TO RELATED APPLICATION

This application claims the benefit under 35 U.S.C. §119 of Korean Patent Application No. 10-2012-0143837, filed on Dec. 11, 2012 in the Korean Intellectual Property Office, the entirety of which disclosure is incorporated herein by reference.

BACKGROUND OF THE INVENTION

1. Field of the Invention

The present invention relates to a multi-dimensional gas chromatography chip, and more particularly to a multi-dimensional gas chromatography chip with a modulator.

2. Description of the Related Art

Chromatography refers to an analysis technology for precisely separating components from a multi-component mixture including not only a simple mixture, but also a very complex mixture.

The chromatography may be variously classified according to types of stationary phases, in particular, types of mobile phases (moving phases).

The chromatography may be classified into a gas chromatography and a liquid chromatography according to types of mobile phases. In the present invention, a description of a liquid chromatography will be omitted.

The gas chromatography technology uses the characteristics in which a trace of a mobile phase is left on a stationary phase according to an attractive force or a suction force of a mixture contained in the mobile phase with respect to the stationary phase if the mobile phase in which the mixture is dispersed is moved through the stationary phase.

That is, according to the gas chromatography technology, the mixture to be separated is contained in the mobile phase.

The mixture components are moved through the stationary phase, and the components constituting the mixture are separated while being moved through the stationary phase.

The gas chromatography is especially convenient, prompt, and highly sensitive, and has a high resolution for a thermally stable volatile material.

By using the chromatography, the components of an arbitrary mixture can be precisely separated.

Then, in the case of a gas chromatography chip for analyzing a very complex mixture, a resolution difference is generated by an entire length of a micro channel, that is, a stationary phase, and a polarity formed in the micro channel (stationary phase).

Meanwhile, a gas chromatography chip manufactured according to the related art employs a dry reactive ion etching (DRIE) technique.

Hereinafter, a method of imprinting a desired pattern on a substrate (wafer) will be briefly described.

In order to imprint a desired pattern on a substrate, (1) a substrate suitable for imprinting a pattern is prepared and a thin film is formed on the substrate by using a material suitable for etching, (2) a pattern to be imprinted on the substrate, that is, a design is prepared, and (3) a desired pattern is imprinted by removing an unnecessary portion from the thin film formed on the substrate according to the pattern drawn in the design by using etching equipment.

The imprinting of a pattern may be classified into a dry etching technique and a wet etching technique.

The DRIE technique is a dry etching technique, in which an etching gas that reacts with a substrate (wafer) is converted into a plasma state and the etching gas having the plasma state collides with the substrate to etch a portion of the substrate through the combination of a physical impact and a chemical reaction between the etching gas and components of the substrate.

The dry etching technique uses a complex apparatus, which makes the technique troublesome and causes excessive costs.

Meanwhile, a wet etching technique refers to a technology of allowing chemicals or chemical materials to flow on a surface of a substrate to remove an unnecessary portion from a thin film formed on the surface of the substrate, and can employs a relatively simple and inexpensive apparatus as compared with the dry etching technique.

According to the gas chromatography chip of the related art, when the mixture serving as the mobile phase is separated, some limitations are represented in the peak resolution, that is, the sensitivity is not high, so that the gas chromatography chip according to the related art is not suitable when stereoscopic gas mixtures are analyzed through the multi-dimensional gas chromatography analysis.

A technology related to the present invention is disclosed in Korean Patent Registration No. 10-0243995 (issued on Feb. 1, 2000).

SUMMARY OF THE INVENTION

Accordingly, the present invention has been made keeping in mind the above problems occurring in the prior art, and an object of the present invention is to provide a multi-dimensional gas chromatography chip with a modulator, which can analyze gas mixtures with high sensitivity by refocusing the peak.

Another object of the present invention is to provide a multi-dimensional gas chromatography chip having high economic efficiency and endurance by employing a wet etching technique.

The objects of the present invention are not limited to the above-mentioned objects, and other objects will be clearly understood by those skilled in the art.

In order to accomplish the above objects, there is provided a multi-dimensional gas chromatography chip including a chip body prepared by sequentially bonding a first substrate, a second substrate and a third substrate; first micro channel pattern parts including first micro channels formed on opposite surfaces of the first and second substrates while facing each other; second micro channel pattern parts including second micro channels formed on opposite surfaces of the second and third substrates while facing each other; a gas inlet formed on one side of one surface of the first substrate, which is opposite to the surface where the first micro channel is formed, to supply a mobile phase; a gas outlet formed on an opposite side of the one surface of the first substrate, which is opposite to the surface where the first micro channel is formed, to discharge the mobile phase; position alignment markers formed on the surface of the first substrate where the first micro channel is formed, both surfaces of the second substrates and the surface of the third substrate where the second micro channel is formed; a first stationary phase spin-coated between the first and second substrates and a second stationary phase spin-coated between the second and third substrates; and a modulator provided in a region serving as an inlet side of the first micro channel pattern parts formed on the first and second substrates as well as an outlet side of the second micro channel pattern parts formed on the second and third substrates.

Preferably, a material of the first to third substrates may include one selected from the group consisting of a glass wafer, a quartz wafer, a polydimethylsiloxane wafer, a silicon wafer, a silicate wafer, a borosilicate wafer, and a fused silica wafer.

In addition, the gas inlet may have a tapered shape, in which a gas supply side has a wide width and a width thereof is gradually narrowed toward the first micro channel pattern parts, the first and second micro channel pattern parts may be formed thorough multi-etching by performing etching processes at least three times, and the multi-dimensional gas chromatography chip may further include a heat transfer contact part to control a temperature of the multi-dimensional gas chromatography chip and a temperature control device to control the heat transfer contact part.

The modulator may be a cryogenic cold trap that generates a heat pulse by intermittently injecting cold helium gas or heated helium gas.

In addition, a pattern width of the first micro channel pattern part may be different from a pattern width of the second micro channel pattern part, and the first stationary phase coated on the first micro channel pattern part may be different from the second stationary phase coated on the second micro channel pattern part.

Further, the mobile phase supplied to the gas inlet may pass through the first micro channel pattern part between the first and second substrates, flow through the second micro channel pattern part formed between the second and third substrates and connected to a first through hole formed through the second substrate, and pass through a second through hole, which is formed through the second substrate at the outlet side of the second micro channel pattern part, and the gas outlet of the first substrate formed in a position corresponding to the second through hole. The gas inlet, the gas outlet and the first and second through holes may be formed through an EDM (electrical discharge machining) or a sandblast scheme.

The details of the other embodiments will be contained in the detailed description and the accompanying drawings.

The advantages and/or features of the present invention and a method of achieving them will be apparent with reference to the embodiments together with the accompanying drawings.

However, the present invention is not limited to the embodiments described below, but may be modified in various forms. The embodiments are provided only to fully disclose the present invention and fully inform those skilled in the art to which the present invention pertains of the scope of the present invention, and is defined only by the claims.

The same reference numerals denote the same elements throughout the specification, and sizes, positions, and coupling relationships of the elements may be exaggerated for clarity.

As described above, according to the exemplary embodiment of the present invention, the multi-dimensional gas chromatography chip having economic efficiency and endurance higher than those of the related art can be provided.

In addition, according to the exemplary embodiment of the present invention, the gas mixtures can be analyzed with ultra-high sensitivity as compared with the related art.

DETAILED DESCRIPTION OF THE INVENTION

Hereinafter, a multi-dimensional gas chromatography chip with a modulator according to exemplary embodiments of the present invention will be described with reference to the accompanying drawings.

First, the basic concept of the present invention will be explained.

Based on the problems occurring in the prior art, inventors of the present invention have found that a gas chromatography chip can be prepared by forming micro channel patterns on transparent substrates through an economic wet etching technique using photo masks having desired patterns and then multi-dimensionally stacking the substrates.

Especially, inventors of the present invention have determined that miniaturization of an apparatus can be expected through the above scheme.

In order to achieve stable high resolution as well as miniaturization of the apparatus, a modulator for adjusting the mobile phase moving in the gas chromatography chip and a cryogenic cold trap are provided. In this case, the gas mixture serving as the mobile phase can be secondarily separated and the retention time of the gas mixture in the gas chromatography chip can be desirably adjusted.

That is, the inventors of the present invention have determined that the high resolution of the gas mixture is possible by refocusing the peak after secondarily separating the gas mixture serving as the mobile phase.

Figure 1:
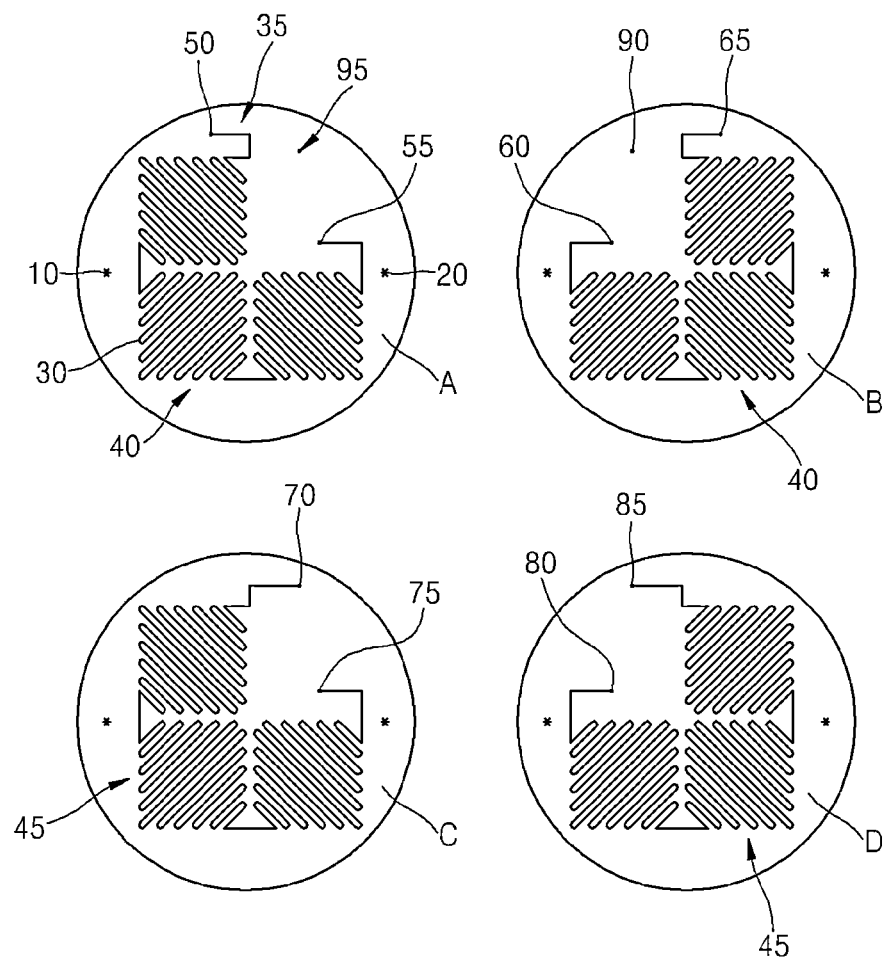
FIG. 1 is a plan view showing photo masks formed with four different micro channel pattern parts, respectively, to form a multi-dimensional gas chromatography chip according to an exemplary embodiment of the present invention.

FIG. 1 is a plan view showing photo masks formed with four different micro channel pattern parts, respectively, to form a multi-dimensional gas chromatography chip according to an exemplary embodiment of the present invention.

In FIG. 1, photo masks A to D are formed with desired micro channel pattern parts, respectively, and subject to multi-etching.

As described above, wet etching is employed in the exemplary embodiment of the present invention and the wet etching is generally known to those having ordinary skill in the art, so detailed description thereof will be omitted.

The photo masks A and B are symmetrical to each other and the photo masks C and D are also symmetrical to each other.

In this manner, when the photo masks A and B and C and D are symmetrically formed, etched chips can be infinitely stacked.

Thus, the length of the micro channel formed in the photo masks can be infinitely extended.

The photo mask A includes position alignment markers 10 and 20, a micro channel pattern part 40 including a micro channel 30, a gas inlet 50 formed at one end of the micro channel pattern part 40, a gas introduction part 35 extending from the gas inlet 50 to the micro channel 30 of the micro channel pattern part 40, a first gas outlet 55 formed at the other end of the micro channel pattern part 40, and a gas outlet 95.

The position alignment markers 10 and 20 are formed at both sides of the photo mask A to align substrates in the process of multi-etching.

The number and position of the position alignment markers 10 and 20 may not be limited to those illustrated in the drawing.

For instance, the position alignment markers 10 and 20 may be formed to the left and right of the photo mask A, and two position alignment markers 10 and 20 may be formed at upper and lower portions of the photo mask A. In addition, the position alignment markers 10 and 20 may be formed at a left portion and a lower portion of the drawing, or the position alignment markers 10 and 20 may be formed at four corners of the drawing, respectively.

In short, the position alignment markers 10 and 20 can be located in various positions to the extent that they do not interfere with the manufacturing process for the micro channel pattern part 40 and the chip.

Alternatively, a cutting surface can be formed by partially cutting the photo mask A and the position of the substrates can be aligned based on the cutting surface.

A connector, such as Nanoport Assembly (R) (manufacturer: UpChurch Scientific (U.S.A.)) can be installed at the gas inlet 50 and the gas outlet 90.

Since the connector is a polyether ether ketone (PEEK) material, it satisfies a condition of a desired thermal resistance (m.p.=340° C.) and a gas is not leaked from an interior of the chip even when a high pressure is applied to the multi-dimensional gas chromatography chip according to the exemplary embodiment of the present invention.

The micro channel pattern part 40 formed in the photo mask A substantially covers an entire surface of the photo mask A, and a predetermined pattern is previously formed.

The micro channel 30 formed in the photo mask A has a width of 100 μm. Thus, when the wet etching is performed with respect to the substrate by using the photo mask A, it is expected that the micro channel pattern part 40 also has a width of 100 μm.

The gas inlet 50 extending to the micro channel 30 in FIG. 1 preferably has a tapered shape.

The tapered shape will be described later with reference to FIG. 4.

The photo mask A may be formed on one surface of the first substrate when the first substrate is etched.

The first gas outlet 55, which is the other end of the micro channel pattern part 40 constituting the photo mask A is connected to a first gas outlet 60 which is the other end of the micro channel pattern part constituting the photo mask B and having a shape and a width the same as those of the micro channel pattern part 40.

In the following description of the photo masks B, C and D, the structure the same as that of the photo mask A may be omitted.

Meanwhile, a position of a gas inlet 65 of the photo mask B corresponds to a position of the gas inlet of the photo mask A.

In the same way, a position of the first gas outlet 60 of the photo mask B corresponds to a position of the gas outlet 55 of the photo mask A.

In addition, as described above, a shape of the micro channel pattern part of the photo mask B is the same as a shape of the micro channel pattern part 40 of the photo mask A.

A gas outlet 90 formed in the photo mask B is positioned corresponding to a gas outlet 95 of the photo mask A.

The photo mask B can be used to etch one surface of the second substrate when the second substrate is etched.

Although it may be described later, preferably, a modulator is provided at a location corresponding to the first gas outlet 55 on a surface of a first substrate 100 where the micro channel pattern part 40 is not formed.

Referring to FIG. 1, the photo mask C includes a first gas inlet 75 connected to the first gas outlet 60 of the photo mask B, a micro channel pattern part 45 having one end extending from the first gas inlet 75, and a second gas outlet 70 formed at the other end of the micro channel pattern part 45.

It should be noted that the width of the micro channel pattern part 45 is different from the width of the micro channel pattern part 40.

For instance, the width of the micro channel pattern part 40 of the photo masks A and B is 100 μm, and the width of the micro channel pattern part 45 of the photo masks C and D is 200 μm.

A second gas outlet 70 of the photo mask C is connected to a second gas outlet 85 of the photo mask D.

The reason to form the width of the micro channel pattern part 45 wider than the width of the micro channel pattern part 40 is to allow the flow of the mobile phase flowing through the micro channel pattern part 40 to be slower than the flow of the mobile phase flowing through the micro channel pattern part 45.

Since the flow of the mobile phase flowing through the micro channel pattern part 40 is slow, the retention time of the mobile phase in the micro channel pattern part 40 may be increased.

In this manner, the multi-layer structure including the micro channel pattern part 40 and the micro channel pattern part 45 may lengthen the moving path of the mobile phase as compared with the structure including the single micro pattern part, so the retention time can be also increased.

Referring to FIG. 1, the photo mask D includes a first gas inlet 80 and a second gas outlet 85.

The position of the first gas inlet 80 corresponds to the position of the first gas inlet 75 of the photo mask C and the position of the second gas outlet 85 corresponds to the position of the second gas outlet 70 of the photo mask C.

The second gas outlet 85 of the photo mask D is connected to the gas outlet 95, which is formed in the photo mask A so as to be formed in the first substrate, by way of a through hole formed through the second substrate, which will be described later.

Hereinafter, the flowing path of the mobile phase will be described with reference to FIG. 1. The gas mixture serving as the mobile phase is introduced into the gas inlet 55 of the photo mask A and the gas inlet 65 of the photo mask B and then discharged through the first gas outlet 55 of the first photo mask A and the first gas outlet 60 of the photo mask B by passing through the gas introduction part 35 and the micro channel pattern part 40 including the micro channel 30.

The mobile phase discharged from the first gas outlets 55 and 60 are introduced into the first gas inlet 75 formed in the photo mask C and the first gas inlet 80 connected to the first gas inlet 75 through the through hole and the discharged through the gas outlet 95 formed in the first substrate 100 by way of the micro channel pattern part 45, the second gas outlet 70 of the photo mask C, the second gas outlet 85 of the photo mask D and the through hole formed through the second substrate 200.

Figure 2:
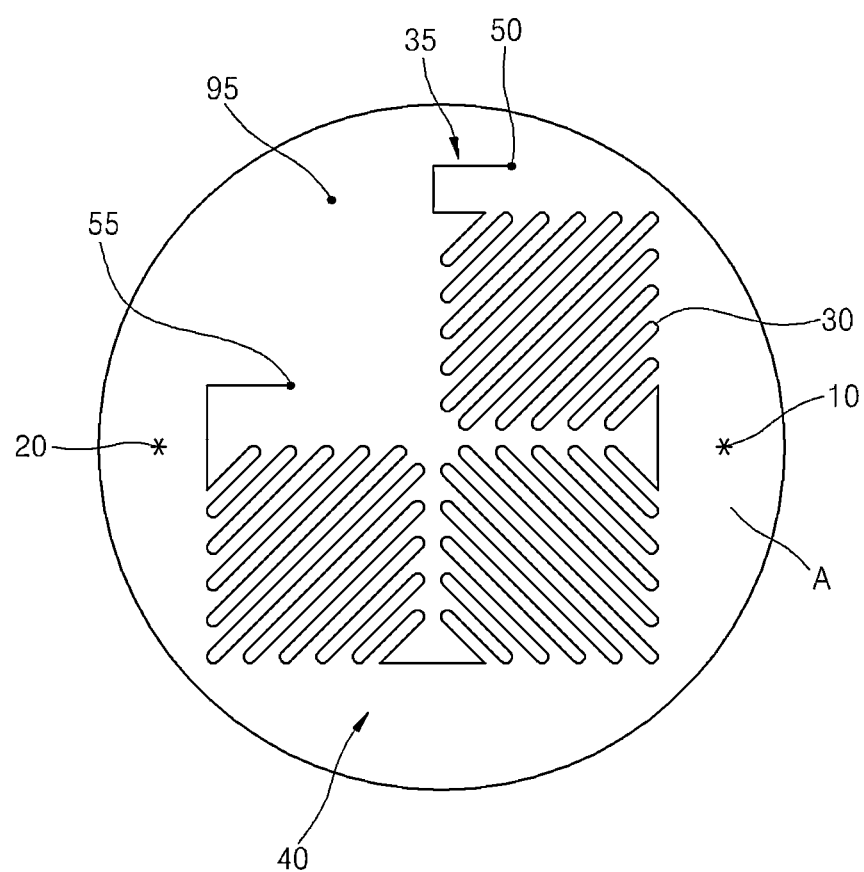
FIG. 2 is a plan view showing a state in which four different micro channel pattern parts of FIG. 1 are formed on substrates through etching and the substrates are bonded with each other according to an exemplary embodiment of the present invention.

FIG. 2 is a plan view showing a state in which four different micro channel pattern parts of FIG. 1 are formed on substrates through etching and the substrates are bonded with each other according to an exemplary embodiment of the present invention.

As can be understood from FIG. 2 showing the plan view of the multi-dimensional gas chromatography chip according to an exemplary embodiment of the present invention, the multi-dimensional gas chromatography chip, similar to the photo mask A of FIG. 1, includes position alignment markers 10 and 20, the micro channel pattern part 40 including the micro channel 30, the gas inlet 50 formed at one end of the micro channel pattern part 40, the gas introduction part 35 extending from the gas inlet 50 to the micro channel 30 of the micro channel pattern part 40, the first gas outlet 55 formed at the other end of the micro channel pattern part 40, and the gas outlet 95.

Figure 3:
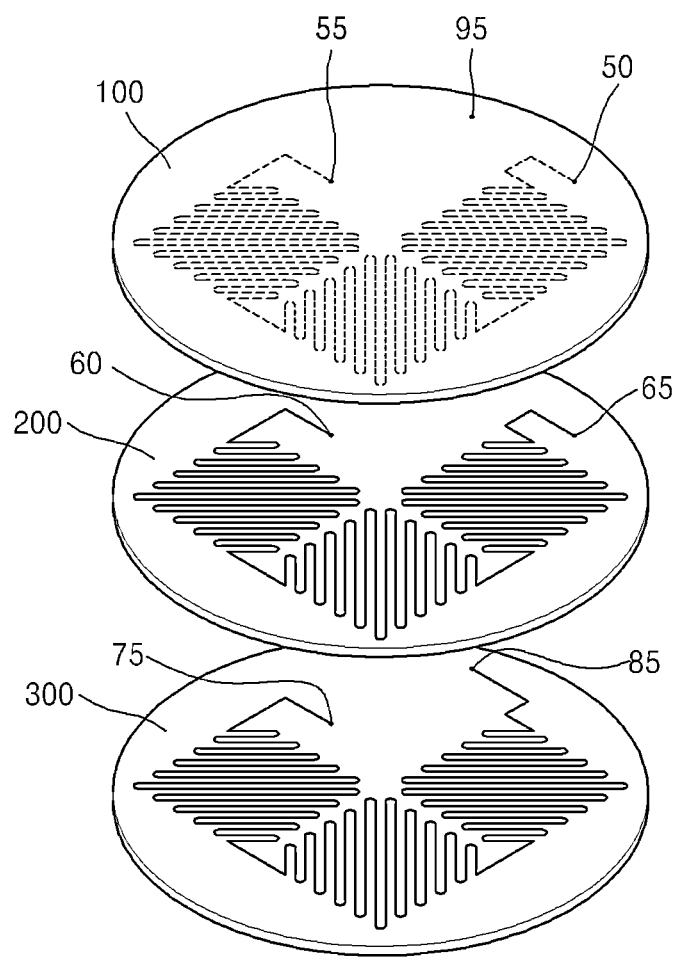
FIG. 3 is a schematic perspective view showing a bonding relationship of substrates when four different micro channel pattern parts of FIG. 1 are formed on substrates through etching and the substrates are bonded with each other according to an exemplary embodiment of the present invention.

FIG. 3 is a schematic perspective view showing a bonding relationship of the substrates when four different micro channel pattern parts of FIG. 1 are formed on substrates through etching and the substrates are bonded with each other according to an exemplary embodiment of the present invention.

As can be understood from FIG. 3, the multi-dimensional gas chromatography chip according to the exemplary embodiment of the present invention includes the first substrate 100 located at the upper portion of the chip, the second substrate 200 located at the middle portion of the chip and the third substrate 300 located at the lower portion of the chip.

The micro channel pattern part 40 of the photo mask A shown in FIG. 1 is formed on the bottom surface of the first substrate 100 through etching and the gas inlet 50 and the gas outlet 95 are formed on the top surface of the first substrate 100.

The micro channel pattern part 40 of the photo mask B shown in FIG. 1 is formed on the top surface of the second substrate 200 through etching and the micro channel pattern part 45 of the photo mask C shown in FIG. 1 is formed on the bottom surface of the second substrate 200 through etching.

The micro channel pattern part 45 of the photo mask D shown in FIG. 1 is formed on the top surface of the third substrate 300 through etching.

As described above, the pattern width of the micro channel pattern part 40 is different from the pattern width of the micro channel pattern part 45.

Therefore, the pattern width of the micro channel pattern part 40 formed on the top surface of the second substrate 200 is different from the pattern width of the micro channel pattern part 45 formed on the bottom surface of the second substrate 200.

It can be clearly understood from FIG. 3 that the gas mixture serving as the mobile phase introduced into the gas inlet 50 continuously flows by way of the gas inlet 50 of the first substrate 100→the first gas outlet 60 of the second substrate 200→the second gas outlet 85 of the third substrate 300→the through hole formed in the second substrate 200 (the through hole connecting the second gas outlet 70 with the corresponding gas outlet 90)→the gas outlet 95 of the first substrate 100.

Figure 4:
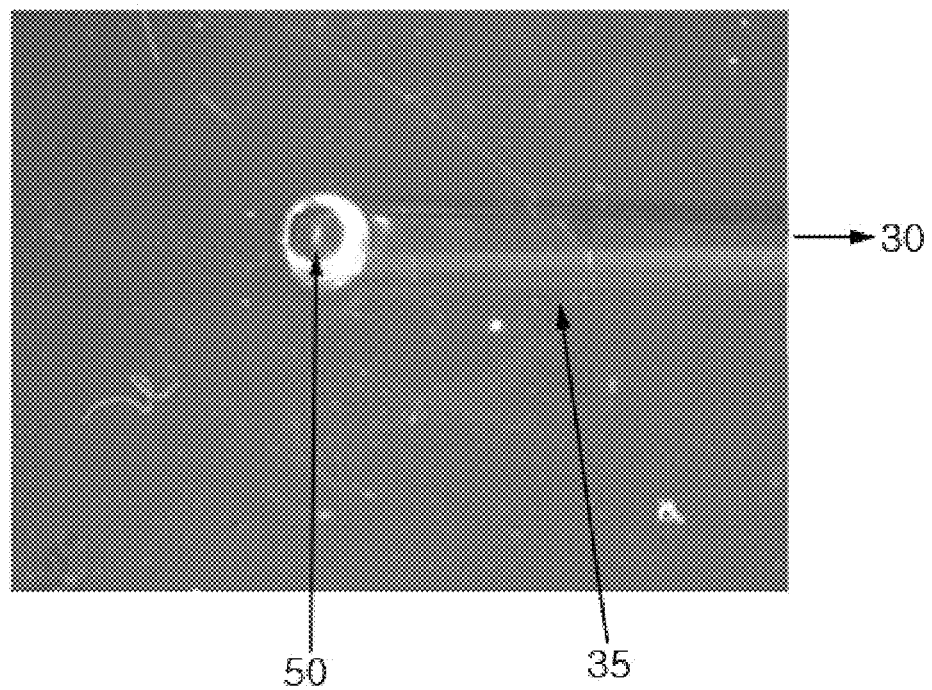
FIG. 4 is a photographic view showing a tapered shape of a gas introduction part formed in a multi-dimensional gas chromatography chip according to an exemplary embodiment of the present invention.

FIG. 4 is a photographic view showing the tapered shape of the gas introduction part formed in the multi-dimensional gas chromatography chip according to an exemplary embodiment of the present invention.

A middle portion in FIG. 4 represents the gas inlet 50 and a right portion in FIG. 4 represents the gas introduction part 35 connected to the micro channel 30 of the micro channel pattern part 40 formed in the multi-dimensional gas chromatography chip shown in FIG. 2.

As can be understood from FIG. 4, a width of the gas introduction part 35 is wide at the side of the gas inlet 50 and a width of a right portion of the gas introduction part 35 is narrow.

Since the fluid path from the gas inlet 50 to the gas introduction part 35 is tapered, the mobile phase can be more easily detected at the gas outlet 95.

Figure 5:
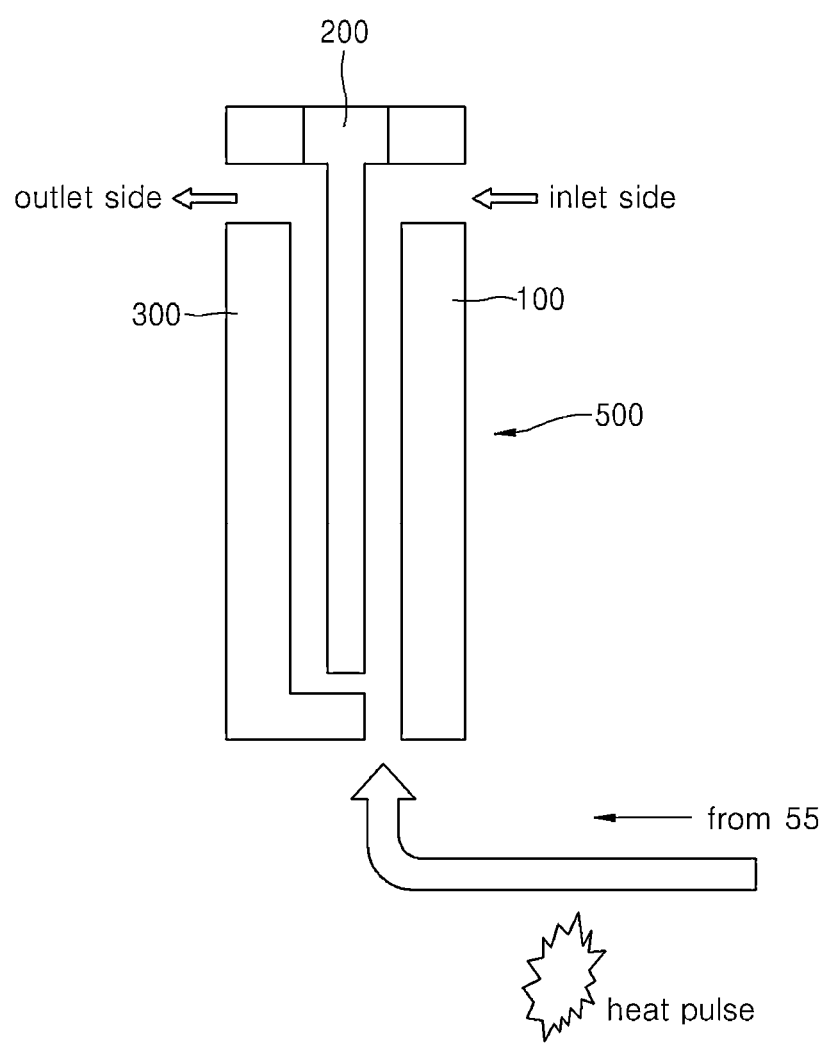
FIG. 5 is a sectional view of a multi-dimensional gas chromatography chip according to an exemplary embodiment of the present invention to illustrate the schematic structure and the operational scheme of a cryogenic cold trap.

FIG. 5 is a sectional view of a multi-dimensional gas chromatography chip according to an exemplary embodiment of the present invention to illustrate the schematic structure and the operational scheme of the cryogenic cold trap.

Referring to FIG. 5, the multi-dimensional gas chromatography chip 500 according to the exemplary embodiment of the present invention includes the first substrate 100 located to the right, the second substrate 200 located at the center, and the third substrate 300 located to the left.

As indicated by an arrow, the modulator is integrally formed with the first gas outlet 55 at the lower end of the multi-dimensional gas chromatography chip 500.

The multi-dimensional gas chromatography chip 500 according to the exemplary embodiment of the present invention can be actually implemented with the modulator.

The modulator may serve as the cryogenic cold trap. The function of the cryogenic cold trap will be described in detail later.

In addition, a structure for applying the heat pulse is illustrated at the lowermost portion in FIG. 5. The heat pulse corresponds to the intermittent function of the cryogenic cold trap applied from the modulator and the configuration of the heat pulse will be described later together with the function of the cryogenic cold trap.

Referring to FIG. 5, the mobile phase is introduced into the inlet side illustrated to the right of the drawing. The mobile phase flows to the lower portion of the second substrate 200 by passing through a gap between the first and second substrates 100 and 200 and the mobile phase that has passed through the lower portion of the second substrate 200 is discharged through the outlet side by passing through a gap between the second and third substrates 200 and 300 illustrated to the left of the drawing.

Figure 6:
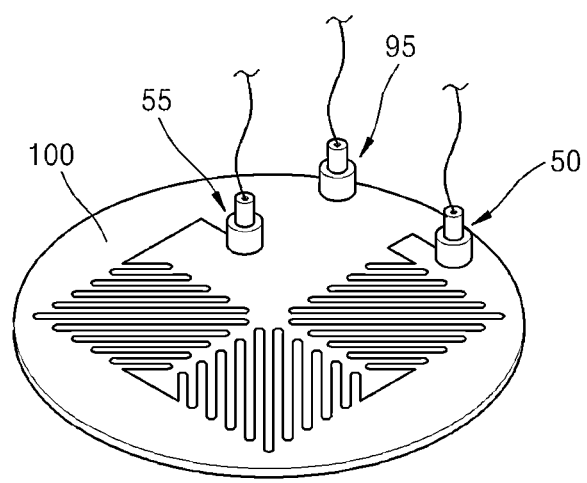
FIG. 6A is a photographic view showing an upper portion of a multi-dimensional gas chromatography chip manufactured according to an exemplary embodiment of the present invention and FIG. 6B is an enlarged view of FIG. 6A.
Figure 6:
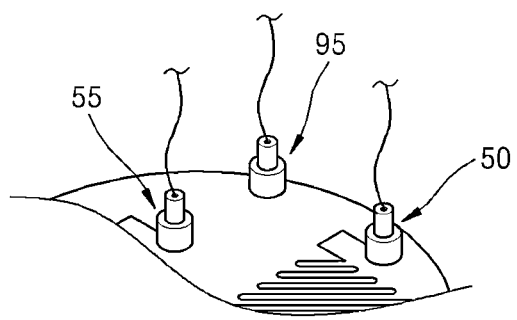

FIG. 6A is a photographic view showing an upper portion of the multi-dimensional gas chromatography chip manufactured according to an exemplary embodiment of the present invention and FIG. 6B is an enlarged view of FIG. 6A.

Referring to FIGS. 6A and 6B, connectors are connected to the gas inlet 50, the gas outlet 95 and the first gas outlet 55, respectively.

In FIGS. 6A and 6B, two connectors illustrated at the upper portion of the drawing serve as the gas inlet and the gas outlet and the connector illustrated at the center of the drawing serves as the modulator.

Figure 7:
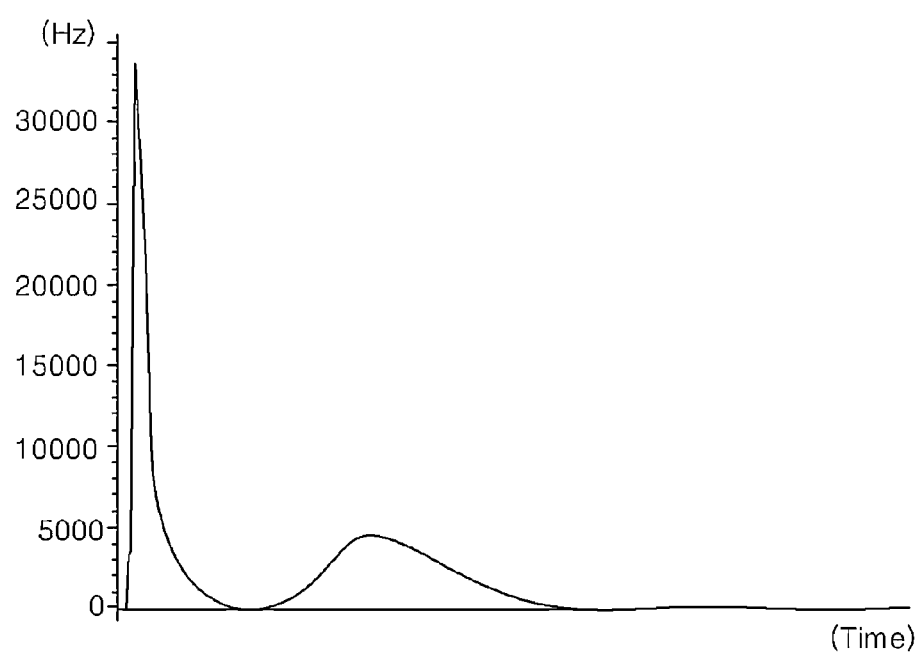
FIG. 7 is a view showing an actual gas analysis result at a trace level of gas mixtures obtained by a multi-dimensional gas chromatography chip according to the exemplary embodiment of the present invention, which represents an ECD detection result of chloroform and 4-bromofluorobenzene.

FIG. 7 is a view showing an actual gas analysis result at a trace level of gas mixtures obtained by a multi-dimensional gas chromatography chip according to the exemplary embodiment of the present invention, which represents an ECD detection result of chloroform and 4-bromofluorobenzene.

In order to obtain a graph of FIG. 7 according to the test result, 9 μl of chloroform and 1 μl of 4-bromofluorobenzene are mixed as analysis samples, and hexane is added to be diluted at a ratio of 1:200.

A μECD detector (model name: HP 6890, manufacturer: Agilent of U.S.A.) was used as analysis equipment.

Other analysis conditions are as follows.
Gas mixture supply temperature: 300° C.
Carrier gas: He
Pressure: 15 MPa
Split ratio: 50:1
Amount of supplied gas: 1 μl
Used column: Micro fab column multilayer (3 m×0.10 mm/0.20 mm), wherein 0.10 mm is a pattern width of the micro channel pattern part 40 and 0.20 mm is a pattern width of the micro channel pattern part 45.
Temperature ramp: 40° C.(1 min)→10° C./min→60° C.(5 min)→15° C./min→120° C.(10 min)→15° C./min→160° C.(5 min)
Temperature of detector: 300° C.

As can be understood from FIG. 7, it is clearly represented that the left peak of the graph is chloroform and it is clearly represented that the right peak of the graph is 4-bromofluorobenzene.

From the peak graph of FIG. 7, it can be understood that the multi-dimensional gas chromatography chip according to the exemplary embodiment of the present invention represents the high resolution of the chloroform and 4-bromofluorobenzene.

Next, a method of implementing the multi-dimensional gas chromatography chip with the modulator according to the exemplary embodiment of the present invention will be described.

Since some parts have been described already, description about redundant parts may be omitted.

1. Preparation of Photo Masks

In order to manufacture the multi-dimensional gas chromatography chip according to the exemplary embodiment of the present invention, photo masks A, B, C and D formed with desired patterns are prepared first.

Preferably, patterns are previously formed in the photo masks A, B, C and D by using a pattern formation program.

For instance, the micro channel pattern parts 40 and 45 shown in FIG. 1 can be formed on the photo masks A, B, C and D, respectively.

After previously forming the micro patterns constituting the micro channel pattern part, the patterns are imprinted on a blank master, which is used as the photo mask when the first to third substrates 100 to 300 are etched for manufacturing the pattern of the multi-dimensional gas chromatography chip according to the present invention.

2. Etching

Those skilled in the art to which the present invention pertains can readily recognize that the desired patterns can be formed on the substrates 100 to 300 by using the photo masks and the photoresist coated on the substrates 100 to 300.

As described above, the width of the micro channel pattern part 40 obtained through the etching according to the exemplary embodiment of the present invention is about 100 μm.

Thus, it is expected that the width of the micro channel pattern part 40 formed on the surfaces of the first and second substrates 100 and 200 may be substantially equal to 100 μm.

Meanwhile, the whole length of the micro channel 30 constituting the micro channel pattern part 40 formed on the surfaces of the first and second substrates 100 and 200 may be increased or decreased depending on the width of the micro channel pattern part 40, especially, the design of the pattern.

Preferably, the material of the substrate is one selected from a glass wafer, a quartz wafer, a polydimethylsiloxane wafer, a silicon wafer, a silicate wafer, a borosilicate wafer, and a fused silica wafer, and most preferably, a borosilicate wafer.

Preferably, the wet etching according to the exemplary embodiment of the present invention is repeatedly performed at least three times until the etching depth reaches about 50 μm.

Referring to FIG. 1, the photo mask A is used for etching one surface of the first substrate 100, the photo mask B is used for etching one surface of the second substrate 200 bonded to the first substrate 100, the photo mask C is used for etching the other surface of the second substrate 200 bonded to the third substrate 300, and the photo mask D is used for etching one surface of the third substrate 300.

Therefore, the photo mask A corresponds to the photo mask B and the photo mask C corresponds to the photo mask D.

Of course, the photo mask B corresponds to the photo mask C. Thus, referring to FIG. 1, the first gas outlet 60 of the photo mask B is located corresponding to the first gas inlet 75 of the photo mask C.

According to the exemplary embodiment of the present invention, the position alignment marks 10 and 20 are formed on the photo masks A, B, C and D, respectively. Thus, when the multi-dimensional gas chromatography chip is manufactured by performing the wet etching processes at least three times, the precise shape and the pattern width of the micro channel pattern parts 40 and 45 can be accurately maintained.

Since the position alignment marks 10 and 20 are formed on the photo masks A, B, C and D, respectively, the first to third substrates 100, 200 and 300 can be accurately aligned with respect to each other after the etching has been finished.

At this time, since the pattern width of the micro channel pattern part 45 needs to be wider than the pattern width of the micro channel pattern part 40, one surface of the second substrate 200 where the micro channel pattern part 45 is formed and one surface of the third substrate 300 where the micro channel pattern part 40 is formed may be subject to the wet etching processes more than three times.

In detail, preferably, the wet etching processes according to the exemplary embodiment of the present invention may repeat until the pattern depth reaches 50 μm.

As a result, the micro channel pattern parts 40 and 45 may preferably have circular sectional shapes.

If the above wet etching scheme is employed, the special technique or equipment required in the conventional DRIE scheme may not be necessary, so the micro channel pattern parts 40 and 45 can be formed in a simple method with an inexpensive cost.

3. Coating of Stationary Phase

Next, polydimethylsiloxane (PDMS) is coated as a stationary phase on opposite surfaces of the first and second substrates 100 and 200.

The PDMS is a material having optically transparent, non-polar and nonflammable property and is coated in a spin coating method by using a spin coater.

For reference, the silicate wafer used in the exemplary embodiment of the present invention is also optically transparent.

Those skilled in the art to which the present invention pertains can readily recognize the spin coating scheme using the spin coater.

According to the exemplary embodiment of the present invention, it is preferred to coat the stationary phase as thin as possible.

In addition, PEG (polyethylene glycol) is coated as a stationary phase on opposite surfaces of the second and third substrates 200 and 300. Similar to the PDMS, it is preferred to coat the PEG as thin as possible.

The reason to coat the PDMS and PEG, respectively, is to allow the mobile phase passing through the micro channel pattern part 40 to have a polarity different from a polarity of the mobile phase passing through the micro channel pattern part 45.

4. Substrate Bonding

After spin-coating the PDMS and PEG serving as the stationary phase, the substrates 100 and 200 and 200 and 300 are bonded with each other through a suitable method.

At this time, the PDMS and PEG may have the function of bonding the substrates 100 and 200 and 200 and 300 as well as the function of sealing bonding surfaces.

For instance, as an example of the bonding method, the bonded substrates 100, 200 and 300 are loaded in an oven and heated for about 1 hour at the temperature of 70° C.

That is, the PDMS and PEG may be simply coated through the spin coating scheme using a spin coater, not by a method, in which after the multi-dimensional gas chromatography chip is formed, the stationary phase is press-injected into the gas inlet 50 or 65 of the micro channel pattern part 40 or 45 to coat a wall surface of the micro channel pattern part 40 or 45, which is technically difficult.

If necessary, a stationary phase having the other polarity may be additionally applied to a coating layer of the substrate.

An example of the stationary phase having the other polarity may include silica gel, alumina, charcoal, a molecular body, and a porous polymer, and when they are applied as a stationary phase, the polarity of the micro channel pattern parts 40 and 45 can be easily adjusted.

As described above, according to the exemplary embodiment of the present invention, since the chip is manufactured not by a dry etching (DRIE) technique according to the related art, but by a wet etching technique, a spin coater having a simple structure with an inexpensive cost can be used so that the process becomes very simple.

According to the exemplary embodiment of the present invention, a specification of the substrate used in the multi-dimensional gas chromatography chip is as follows.

Size of substrate: 4 inches
Size of gas inlet: 600 μm
Size of gas outlet: 600 μm
Channel width of micro channel pattern part 40: 100 μm
Channel width of micro channel pattern part 45: 200 μm
Material of substrate: borosilicate wafer It should be noted that a size of the gas inlet 600 μm and the channel width of the micro channel 30 of the micro channel pattern 40 is 100 μm, and thus, as described above, a fluid path from the gas inlet to the micro channel has a tapered shape.

5. Additional Work

Next, a method of forming the gas inlet 50, the gas introduction part 35 extending from the gas inlet 50, the gas outlet 95, and the through hole formed through the second substrate 200 (an overlap part between the first gas outlet 60 formed in the first photo mask B of FIG. 1 and the first gas inlet 75 formed in the photo mask C of FIG. 1) of the multi-dimensional gas chromatography chip according to the exemplary embodiment of the present invention will be described.

First, it should be noted that the gas inlet 50, the gas introduction part 35, the gas outlet 95, and the through hole may be accurately formed through sand blasting.

However, since sand blasting is very inefficient for small-scale production, according to the exemplary embodiment of the present invention, the gas inlet 50, the gas introduction part 35, the gas outlet 95, and the through hole are formed by using electrical discharge machining (EDM).

Then, 5 M of a KOH solution is prepared, the multi-dimensional gas chromatography chip of the present invention is completely submerged (at 8 mm or deeper) in the KOH solution, and a current of 40 V/3 A is applied.

If necessary, the EDM electrode and the solution are properly replaced.

The gas inlet and the gas outlet may be simultaneously formed on one surface of the gas chromatography chip, or one may be formed on one surface thereof and the other may be formed on an opposite surface thereof.

The former case is convenient for work and the heat transfer part to be described later can be easily attached, and the latter case is advantageous in that it is easy to continuously connect the multi-dimensional gas chromatography chips when a multi-dimensional chromatography chip assembly is formed.

Especially, in the case of the latter, the length of the micro channel can be infinitely increased by connecting a plurality of the multi-dimensional chromatography chips.

6. Connection of External Column

Next, a column for supplying a gas mixture which is to be analyzed is connected to the multi-dimensional gas chromatography chip obtained according to the exemplary embodiment of the present invention.

To this end, as shown in FIGS. 6A and 6B, the connector is connected to the gas inlet 50 and the gas outlet 95 formed at one side of the multi-dimensional gas chromatography chip according to the exemplary embodiment of the present invention.

As described above, two connectors illustrated in the upper portion of FIGS. 6A and 6B may serve as the gas inlet and the gas outlet.

The connector at the side of the gas inlet is in charge of supplying a gas serving as the mobile phase and the connector at the side of the gas outlet may discharge the gas mixture that has passed through the multi-dimensional gas chromatography chip according to the exemplary embodiment of the present invention.

At this time, the gas mixture discharged from the connector at the side of the gas outlet may be supplied again to the connector at the side of the gas inlet of another multi-dimensional gas chromatography chip.

In this case, the movement path of the gas mixture serving as the mobile phase can be lengthened very long, so the gas mixture can be separated with the higher resolution.

In order to measure an analysis performance of the multi-dimensional gas chromatography chip obtained according to the present invention, the present invention may further include detection apparatuses connected to the multi-dimensional gas chromatography chip, for example, a flame ionization detector (FID), an electron capture detector (ECD), and a mass analyzer.

The FID is mainly used for analysis of organic compounds, such as HC, TCE or PCE, and the ECD is mainly used for detection of a compound containing halogen elements (for example, F, Cl, Br, and I) as well as for detection of agricultural chemicals, a PCB, and a $N_2O$ gas.

7. Heat Transfer Part

A heat transfer part may be further formed in the multi-dimensional gas chromatography chip obtained according to the exemplary embodiment of the present invention to control the temperature.

The heat transfer part may be formed in an area where accessories of the multi-dimensional gas chromatography chip are not formed, and alternatively, may be formed to heat the entire multi-dimensional gas chromatography chip.

Further, as described above, the temperature control unit may be preferably further installed in the heat transfer part.

Thus, in the case of the multi-dimensional gas chromatography chip according to the present invention, since the temperature of the multi-dimensional gas chromatography chip can be controlled rapidly or precisely by the temperature control unit, the temperature can be controlled immediately and effectively as compared with the gas chromatography technique according to the related art, and thus, a very clear peak can be obtained when the gas mixture is analyzed at the trace level.

The heat transfer part may employ a peltier device by taking the small-size of the multi-dimensional gas chromatography chip into consideration.

Further, the heat transfer part controls the temperature of the multi-dimensional gas chromatography chip and applies a thermal pressure to the bonding portion of the multi-dimensional gas chromatography chip to prevent leakage of the gas in the micro channel.

This is because the heat applied to the multi-dimensional gas chromatography chip can apply thermal pressure the mobile phase applied between the substrates so that the bonding force between the substrates can be improved.

8. Modulator

As described above, the modulator may be added to the surface of the substrate 100 where the micro channel pattern part 40 is not formed at the position corresponding to the first gas outlet 55.

Prior to explaining the structure of the modulator, the refocusing effect of the peak for the gas mixture serving as the mobile phase according to the exemplary embodiment of the present invention will be briefly described.

When the gas mixture serving as the mobile phase is introduced into and flows through the multi-dimensional gas chromatography chip, if the gas mixture can be secondarily separated, the refocusing effect of the peak of the gas mixture may be expected.

In this case, especially, if the ultra-low temperature effect is applied to the gas mixture, the movement time of the gas mixture is lengthened so that the analysis time is increased. Thus, the resolution is remarkably improved, so that the analysis for the gas mixture sample at the trace level may be expected.

The structure of the modulator has been briefly described with reference to FIG. 5.

According to the exemplary embodiment of the present invention, the modulator equipped with the cryogenic cold trap, which is the ultra-low temperature apparatus, and the heat pulse function is employed.

The modulator is the ultra-low temperature apparatus and intermittently condenses the gas mixture introduced into the micro channel pattern part 45 and applies the heat pulse to the gas mixture to secondarily analyze the gas mixture.

According to the exemplary operation of the modulator, cold helium gas cooled with liquid nitrogen is firstly supplied and then helium gas heated to the high temperature of 375° C. may be supplied if necessary.

In addition, the cold helium gas and the heated helium gas can be alternately supplied, preferably, at an interval of 1 minute to 2 minutes.

If necessary, the interval may be set in the unit of second, other than in the unit of minute. When taking the time required for cooling or heating the helium gas, it is preferred to supply the helium gas at the interval in the unit of minute.

The helium gas may be heated by a separate heater or flame.

The helium gas can be supplied through the through hole, which is located corresponding to the first gas outlet 55 and formed on an outer surface of the first substrate of the multi-dimensional gas chromatography chip according to the exemplary embodiment of the present invention.

In the multi-dimensional gas chromatography chip according to the exemplary embodiment of the present invention, the mobile phase flowing through the micro channel pattern part 40 is condensed by the cold helium gas supplied from the modulator and the peak refocusing is carried out by the condensation process.

At this time, as described above, if the heat pulse caused by the cold helium gas and the heated helium gas is alternatively applied at a proper interval, the condensed gas mixture is introduced into and flows through the micro channel pattern part 45, so that the separation is achieved.

If necessary, the local cooling may be performed by using the peltier device.

9. Separation Test for Gas Mixture Sample

The separation test result for the gas mixture has been already described with reference to FIG. 7.

The multi-dimensional gas chromatography chip according to the exemplary embodiment of the present invention can be manufactured in a simple method with an expensive cost and represent the superior resolution, so the multi-dimensional gas chromatography chip can accurately separate the gas mixture at the trace level.

The detailed embodiments of the present invention have been described until now, but the present invention can be variously modified without departing from the scope of the present invention.

Accordingly, the scope of the present invention should not be limited to the embodiments, but should be determined according to both the claims and their equivalents.

Although the present invention has been described with reference to the embodiments and the drawings, the present invention is not limited to the embodiments, but those skilled in the art to which the present invention pertains can make various modifications and changes from the description.

Therefore, the spirit of the present invention should be recognized by the claims, and their equivalent modifications fall in the scope of the present invention.

What is claimed is:

1. A multi-dimensional gas chromatography chip comprising:
a chip body prepared by sequentially bonding a first substrate, a second substrate and a third substrate;
first micro channel pattern parts including first micro channels formed on opposite surfaces of the first and second substrates while facing each other;
second micro channel pattern parts including second micro channels formed on opposite surfaces of the second and third substrates while facing each other;
a gas inlet formed on one side of one surface of the first substrate, which is opposite to the surface where the first micro channel is formed, to supply a mobile phase;
a gas outlet formed on an opposite side of the one surface of the first substrate, which is opposite to the surface where the first micro channel is formed, to discharge the mobile phase;
position alignment markers formed on the surface of the first substrate where the first micro channel is formed, both surfaces of the second substrates and the surface of the third substrate where the second micro channel is formed;

a first stationary phase spin-coated between the first and second substrates and a second stationary phase spin-coated between the second and third substrates;

a modulator provided in a region serving as an inlet side of the first micro channel pattern parts formed on the first and second substrates as well as an outlet side of the second micro channel pattern parts formed on the second and third substrates;

wherein the mobile phase supplied to the gas inlet passes through the first micro channel pattern part between the first and second substrates, flows through the second micro channel pattern part formed between the second and third substrates and connected to a first through hole formed through the second substrate, and passes through a second through hole, which is formed through the second substrate at the outlet side of the second micro channel pattern part, and the gas outlet of the first substrate formed in a position corresponding to the second through hole; and the gas inlet, the gas outlet and the first and second through holes are formed through an EDM (electrical discharge machining) or a sandblast scheme.

2. The multi-dimensional gas chromatography chip of claim 1, wherein a material of the first to third substrates is one selected from the group consisting of a glass wafer, a quartz wafer, a polydimethylsiloxane wafer, a silicon wafer, a silicate wafer, a borosilicate wafer, and a fused silica wafer.

3. The multi-dimensional gas chromatography chip of claim 1, wherein the gas inlet has a tapered shape, in which a gas supply side has a width and the width thereof is gradually narrowed toward the first micro channel pattern parts, the first and second micro channel pattern parts are formed thorough multi-etching by performing etching processes at least three times, and the multi-dimensional gas chromatography chip further comprises a heat transfer contact part to control a temperature of the multi-dimensional gas chromatography chip and a temperature control device to control the heat transfer contact part.

4. The multi-dimensional gas chromatography chip of claim 3, wherein the modulator is a cryogenic cold trap that generates a heat pulse by intermittently injecting cold helium gas or heated helium gas.

5. The multi-dimensional gas chromatography chip of claim 1, wherein a pattern width of the first micro channel pattern part is different from a pattern width of the second micro channel pattern part, and the first stationary phase coated on the first micro channel pattern part is different from the second stationary phase coated on the second micro channel pattern part.

6. A multi-dimensional gas chromatography chip comprising:

a chip body prepared by sequentially bonding a first substrate, a second substrate and a third substrate;

first micro channel pattern parts including first micro channels formed on opposite surfaces of the first and second substrates while facing each other;

second micro channel pattern parts including second micro channels formed on opposite surfaces of the second and third substrates while facing each other;

a gas inlet formed on one side of one surface of the first substrate, which is opposite to the surface where the first micro channel is formed, to supply a mobile phase;

a gas outlet formed on an opposite side of the one surface of the first substrate, which is opposite to the surface where the first micro channel is formed, to discharge the mobile phase;

position alignment markers formed on the surface of the first substrate where the first micro channel is formed, both surfaces of the second substrates and the surface of the third substrate where the second micro channel is formed;

a first stationary phase spin-coated between the first and second substrates and a second stationary phase spin-coated between the second and third substrates;

a modulator provided in a region serving as an inlet side of the first micro channel pattern parts formed on the first and second substrates as well as an outlet side of the second micro channel pattern parts formed on the second and third substrates;

wherein the gas inlet has a tapered shape, in which a gas supply side has a width, where the width thereof is gradually narrowed toward the first micro channel pattern parts, the first and second micro channel pattern parts are formed thorough multi-etching by performing etching processes at least three times;

the multi-dimensional gas chromatography chip further comprises a heat transfer contact part to control a temperature of the multi-dimensional gas chromatography chip and a temperature control device to control the heat transfer contact part; and wherein the modulator is a cryogenic cold trap that generates a heat pulse by intermittently injecting cold helium gas or heated helium gas.

7. The multi-dimensional gas chromatography chip of claim 6, wherein a material of the first to third substrates is one selected from the group consisting of a glass wafer, a quartz wafer, a polydimethylsiloxane wafer, a silicon wafer, a silicate wafer, a borosilicate wafer, and a fused silica wafer.

8. The multi-dimensional gas chromatography chip of claim 6, wherein a pattern width of the first micro channel pattern part is different from a pattern width of the second micro channel pattern part, and the first stationary phase coated on the first micro channel pattern part is different from the second stationary phase coated on the second micro channel pattern part.

* * * * *